United States Patent
Feng et al.

(10) Patent No.: US 9,659,359 B1
(45) Date of Patent: May 23, 2017

(54) METHOD OF AND DEVICE FOR QUALITY CONTROL PROCESS OPTIMIZATION

(71) Applicant: Flextronics AP, LLC, Broomfield, CO (US)

(72) Inventors: Zhen Feng, San Jose, CA (US); Weifeng Liu, Dublin, CA (US); David Geiger, Dublin, CA (US); Anwar Mohammed, San Jose, CA (US); Murad Kurwa, San Jose, CA (US)

(73) Assignee: Flextronics AP, LLC, Broomfield, CO (US)

( * ) Notice: Subject to any disclaimer, the term of this patent is extended or adjusted under 35 U.S.C. 154(b) by 13 days.

(21) Appl. No.: 14/704,822

(22) Filed: May 5, 2015

(51) Int. Cl.
  *G06K 9/00* (2006.01)
  *G06T 7/00* (2017.01)
  *G06K 9/52* (2006.01)
  *G06T 11/20* (2006.01)

(52) U.S. Cl.
  CPC .............. *G06T 7/0004* (2013.01); *G06K 9/52* (2013.01); *G06T 11/206* (2013.01)

(58) Field of Classification Search
  CPC ........ G06T 7/0004; G06T 11/206; G06K 9/52
  See application file for complete search history.

(56) References Cited

U.S. PATENT DOCUMENTS

2013/0077850 A1* 3/2013 Hirai ..................... G06T 7/0004
  382/149

OTHER PUBLICATIONS

Xu et al, Adaptive Real-Time Fuzzy X-Ray Solder Joint Inspection System, 2002, Journal of Manufacturing Systems vol. 21 / No. 2, pp. 111-125.*
Soukup, 'A Methodology for Optimization of False Call Rate in Automated Optical Inspection Post Reflow,' 2010, IEEE 33rd Int. Spring Seminar on Electronics Technology, pp. 263-267.*

* cited by examiner

*Primary Examiner* — David F Dunphy
(74) *Attorney, Agent, or Firm* — Haverstock & Owens LLP

(57) ABSTRACT

Methods of and Devices for quality control that can be used with automated optical inspection (AOI), solder paste inspection (SPI), and automated x-ray inspection (AXI) are disclosed. Plurality of threshold settings are entered in a testing process. Multiple testing results are obtained from the testing process. A graphic presentation is generated showing the numerical relationship among the data points, such that a quality control person is able to fine-tune the testing process to have a predetermined ratio of Defect Escaped % to False Call ppm.

18 Claims, 5 Drawing Sheets

METHOD OF AND DEVICE FOR QUALITY CONTROL PROCESS OPTIMIZATION

FIELD OF THE INVENTION

The present invention relates to the field of quality control. More specifically, the present invention relates to optimizing product inspecting process and device in a quality control process.

BACKGROUND OF THE INVENTION

Typical method of fine tuning quality control tools and process, such as Automated Optical Inspection (AOI), Solder Paste Inspection (SPI), and Automated x-ray Inspection (AXI), is time consuming and cumbersome, because a typical machine only allows one input for the threshold setting and one output threshold setting for the testing result at each testing time.

FIG. 1 illustrates a typical product inspection process 100. The process 100 starts from Step 102 that an algorithm is chosen and used for controlling the parameters/conditions of the product inspection process 100. At Step 104, threshold setting input is performed. The threshold setting input only allows one criterium or one condition to be entered/setup. At Step 106, a product inspection and testing is performed. At Step 108, results of the testing at the Step 106 are acquired. At Step 110, the results are examined to determine whether the threshold setting meets the quality requirement standards. If the results do not meet the required standards, the process from the Step 110 goes to Step 112. At Step 112, a new threshold setting is performed, such that the old setting at Step 104 is replaced. If the results at Step 110 meet the required quality standard, the Step 110 goes to an end at Step 114.

As described above, the typical product inspection process 100 only allows setting and changing the threshold setting with one value at a time, which results in a slow product examination process.

SUMMARY OF THE INVENTION

In an aspect, a method of performing quality control inspection comprises entering plurality of threshold settings and generating graphic presentation showing a relationship of at least two factors monitored. In some embodiments, the at least two factors comprises a number of a defect escaped and a false call rate. In other embodiments, the number of the defect escaped comprises a percentage of the defect escaped. In some other embodiments, the false call rate comprises a rate of false call ppm. In some embodiments, the quality control inspection comprises an automated optical inspection. In other embodiments, the quality control inspection comprises an automated x-ray inspection. In some other embodiments, the quality control inspection comprises a solder paste inspection. In some embodiments, the method further comprises adjusting the threshold setting numbers based on the relationship. In some other embodiments, the relationship is substantially linear.

In another aspect, a quality control inspection system comprises an optical inspection device, a first set of computer executable instructions stored in a computer configured to receive plurality of threshold setting numbers, and a second set of computer executable instruction stored in the computer configured to operate the optical inspection element.

In some embodiments, the plurality of threshold setting numbers comprises at least three numbers. In other embodiments, the optical inspection device comprises an automated optical inspection device. In some other embodiments, the optical inspection device comprises a solder paste inspection device. In some embodiments, the optical inspection device comprises an automated x-ray inspection device. In some other embodiments, the system further comprises a third set of computer executable instruction configured to plot data received from testing into data points on a chart showing the numeral relationship among the data points.

In another aspect, a method of inspecting an electronic circuit member comprises requesting one or more inputs of at least two threshold settings, performing a testing of electronic circuit inspection, receiving data of the testing, and generating a graphic presentation showing a numerical relationship between a plurality of data points.

In some embodiments, the data points are in a substantial linear relationship. In other embodiments, the testing comprises an optical inspection. In some other embodiments, the method further comprises selecting an algorithm of the testing. In some embodiments, the method further comprises adjusting the inputs of the at least two threshold settings.

Other features and advantages of the present invention will become apparent after reviewing the detailed description of the embodiments set forth below.

BRIEF DESCRIPTION OF THE DRAWINGS

Embodiments will now be described by way of examples, with reference to the accompanying drawings which are meant to be exemplary and not limiting. For all figures mentioned herein, like numbered elements refer to like elements throughout.

DETAILED DESCRIPTION OF THE PREFERRED EMBODIMENT

Reference is made in detail to the embodiments of the present invention, examples of which are illustrated in the accompanying drawings. While the invention is described in conjunction with the embodiments below, it is understood that they are not intended to limit the invention to these embodiments and examples. On the contrary, the invention is intended to cover alternatives, modifications and equivalents, which can be included within the spirit and scope of the invention as defined by the appended claims. Furthermore, in the following detailed description of the present invention, numerous specific details are set forth in order to more fully illustrate the present invention. However, it is apparent to one of ordinary skill in the prior art having the benefit of this disclosure that the present invention can be practiced without these specific details. In other instances, well-known methods and procedures, components and processes have not been described in detail so as not to unnecessarily obscure aspects of the present invention. It is, of course, appreciated that in the development of any such actual implementation, numerous implementation-specific decisions must be made in order to achieve the developer's specific goals, such as compliance with application and business related constraints, and that these specific goals vary from one implementation to another and from one developer to another. Moreover, it is appreciated that such a development effort can be complex and time-consuming, but is nevertheless a routine undertaking of engineering for those of ordinary skill in the art having the benefit of this disclosure.

Figure 1:
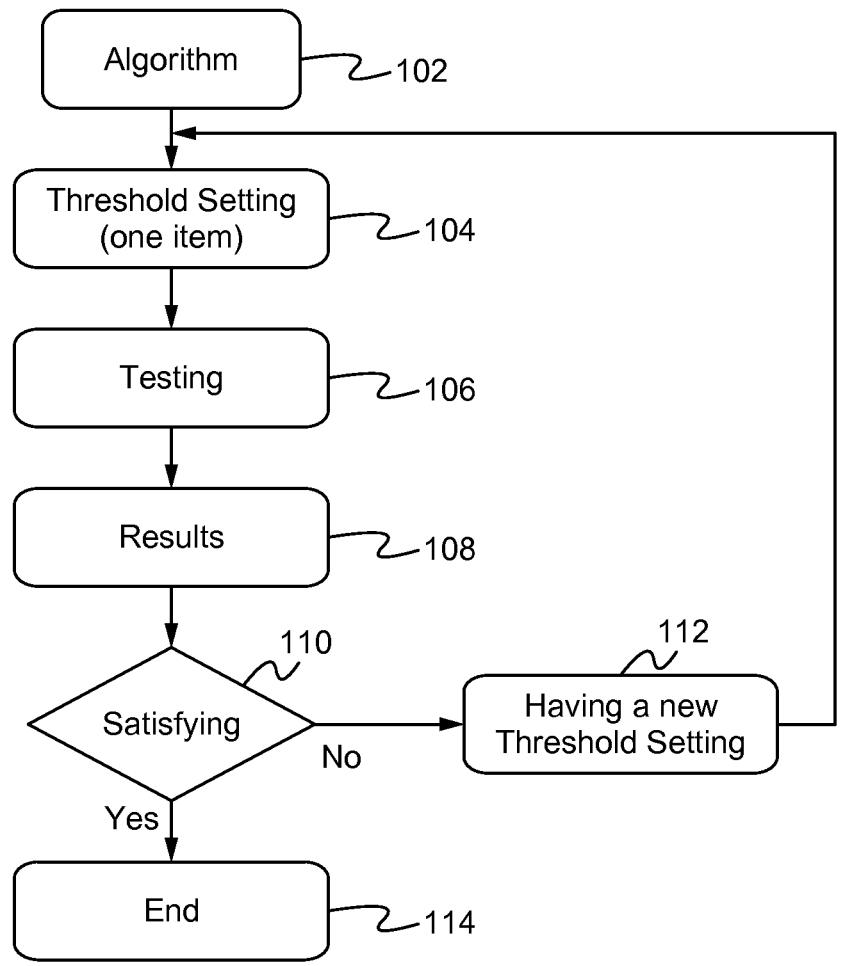
FIG. 1 illustrates a typical product inspection process.
Figure 2:
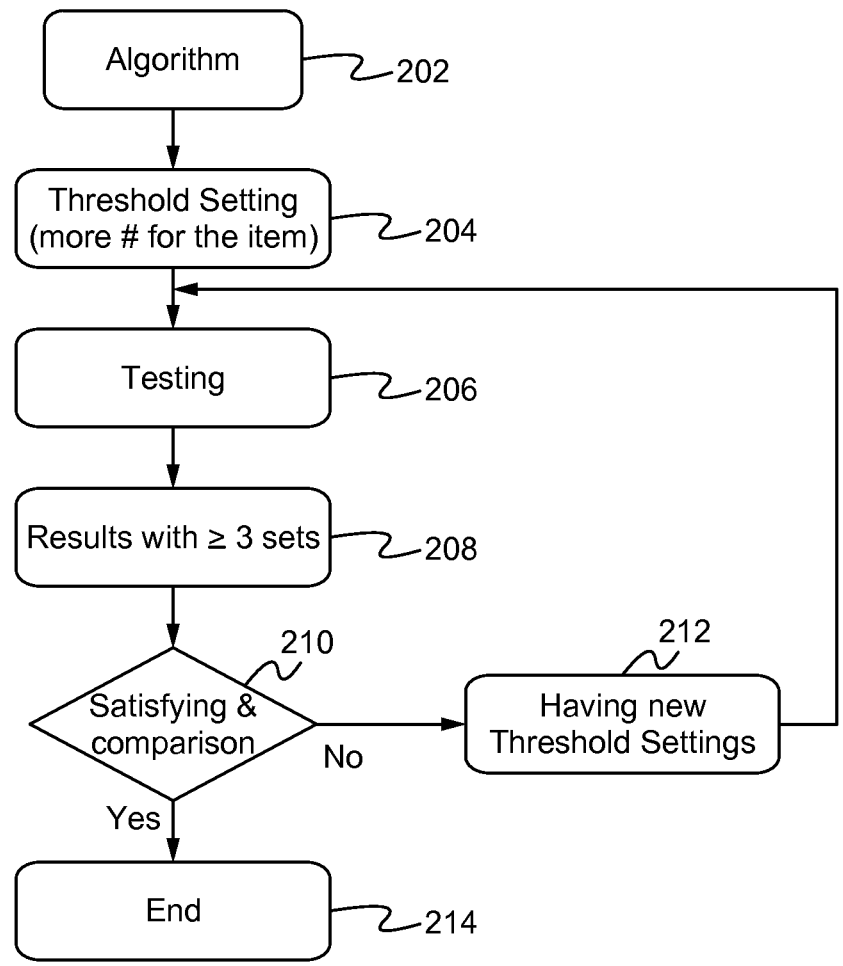
FIG. 2 illustrates an inspection process in accordance with some embodiments of the present invention.

FIG. 2 illustrates an inspection process 200 in accordance with some embodiments of the present invention. The process 200 starts from Step 202 that an algorithm is chosen and used for controlling the parameters/conditions of the product inspection process 200. At Step 204, plurality of threshold setting inputs (including ranges of one or more parameters) are performed/entered. For example, a threshold range between +3% and −3% is entered. In another example, a first threshold range between +1% and −1% and a second threshold range between +3% and −3% are entered. The two ranges can show different quality standards/quality control as needed for statistic analysis. The threshold settings can be one or more pre-defined numbers or a range of numbers. At Step 206, product inspections and/or testings are performed.

At Step 208, results of the testing at the Step 206 are acquired/obtained. In some embodiments, at least three sets of results are generated. In some embodiments, the results contain numerical data that are converted into one or more computer generated graphic charts/figures. The charts comprise a bar graph, a pie graph, or any other graph representations, such that a person of ordinary skilled in the art is able to visually apprehend the testing results. For example, a graphic chart of Defect Escaped Percentage (DE %) versus False Call ppm (Fppm) for individual testing. False Call ppm refers to the false call parts (pins) per million. False Call ppm can be represented by the formula ppm=[(False call pin number)/(Total tested pin number)]×1,000,000. Defect Escaped Percentage (DE %) refers to the percentages of the defect that is escaped from quality screening check.

At Step 210, checking result satisfaction and comparison are performed. In the event if the results do not meet the predetermined quality control standards, the process goes to Step 212. At Step 212, new threshold settings are requested to be inputted. Once the new threshold settings are entered, the method 200 goes to Step 206 for performing the testing and the remaining cycle again. In the event if the results meet the quality control standard at Step 210, the method 200 goes to stop at Step 214.

Figure 3:
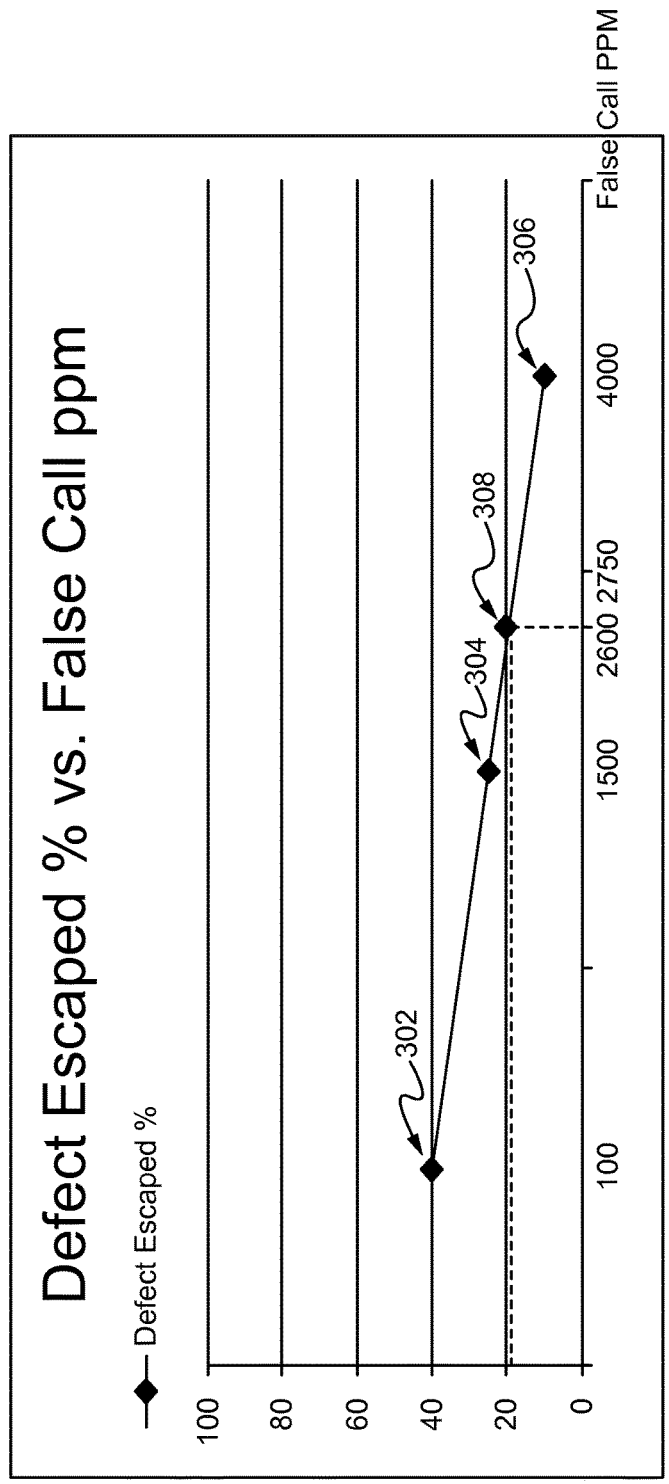
FIG. 3 illustrates a chart of Defect Escaped Percentage (DE %) versus False Call ppm (Fppm) for an individual testing in accordance with some embodiments of the present invention.

FIG. 3 illustrates a chart 300 of Defect Escaped Percentage (DE %) versus False Call ppm (Fcppm) for an individual testing in accordance with some embodiments of the present invention. The chart 300 illustrates the testing results presented in a dot-line graph. The data point 302 shows that the Defected Escaped % is 40 when the False Call ppm is 100. The data point 304 shows that the Defected Escaped % is 25 when the False Call ppm is 1500. The data point 306 shows that the Defected Escaped % is 10 when the False Call ppm is 4000.

As shown in the chart 300, a higher percentage of defects are escaped when a lower False Call rate is chosen. An user is able to choose a predetermined defect escaped % based on the linear relationship with the False Call ppm via the visual presentation of the chart. For example, if a user or a person of quality control wants to choose a defect escape rate not higher than 20% (data point 308), a False Call ppm that is equal or great than 2600 is expected. By using the chart 300, an user is able to find a balance of the false call rate and the quality of the inspection (e.g., the percentage of defects escaped).

In an example, an AXI is performed. An open outlier threshold is set to less or equal to −3. Another two inputs, such as +/−20% is chosen, < or =−3.6 and < or =−2.4 are chosen. A graph like chart 300 can be generated.

Figure 4:
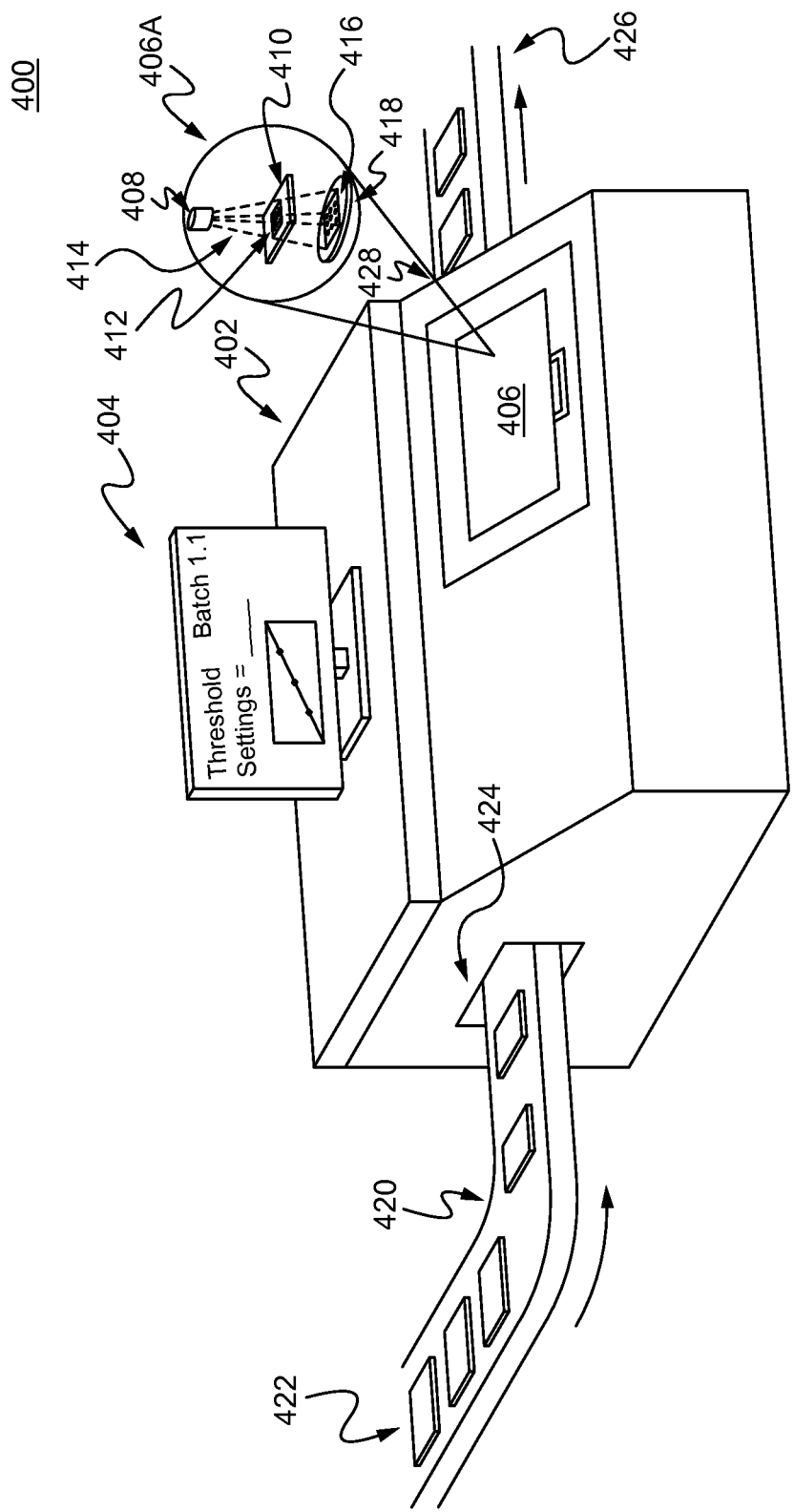
FIG. 4 illustrates an inspection device in accordance with some embodiments of the present invention.

FIG. 4 illustrates an inspection device 400 in accordance with some embodiments of the present invention. The device 400 comprises a testing/examining portion 402 and a display 404. The testing portion 402 comprises a sample load chamber 406. Inspecting elements 406A are within the chamber 406. The inspecting elements 406A comprise a light source 408, such as an x-ray emitter, a sample holder 410, and a image/data receiver 418. A selected inspection light 414 is applied on the sample 412 on the holder 410, which results in an examined image/data 416 on the receiver 418.

The examined image/data 416 is received, analyzed, and calculated by a computing device loaded with computer executable instructions, computer software, and/or non-transitory computer-readable media. One or more graphs are plotted showing the numerical relationships among the data points, such that an operational person is able to visualize the testing results.

In some embodiments, a conveying belt system 420 provides an automatic sampling function. Samples, such as IC chips 422, are automatically sent into the testing portion 402 via input port 424. The tested chips 426 come out from the output port 428.

Figure 5:
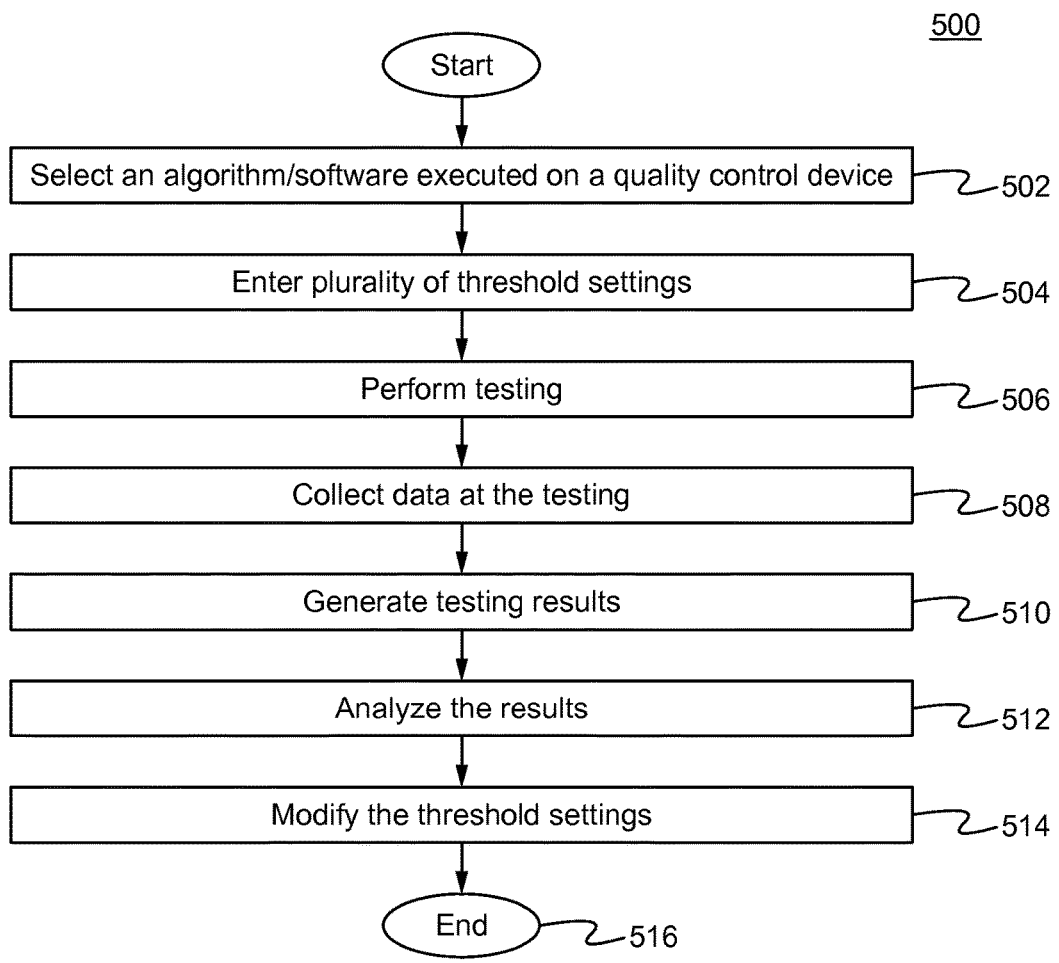
FIG. 5 is a flow chart illustrating a quality control method in accordance with some embodiments of the present invention.

FIG. 5 is a flow chat illustrating a quality control method 500 in accordance with some embodiments of the present invention. At Step 502, an algorithm/software application is selected and executed on a quality control device. For example, the software is used on the Automated X-ray inspection (AXI), which is based on the same/similar principles as automated optical inspection (AOI). AXI uses X-rays as its source to automatically inspect features of ICs (integrated circuit) with packages such as BGAs (ball grid array). In some embodiments, the algorithm/software application is installed and executed on a testing device paired with AXI for functional and structural testing. In some embodiments, the algorithm/software application is installed and executed on a testing device paired with SPI (Solder Paste Inspection) for solder paste testing.

At Step 504, plurality of threshold settings are entered. At Step 506, testing is performed. At Step 508, testing data are collected. At Step 510, testing results are generated. In some embodiments, the testing results are presented in a graph allowing people to visually determine whether the settings result in a linear relationship, a bell curve relationship, or any other numerical relationships. At Step 512, the results are analyzed and predictions are made for the adjustments of the threshold settings. At Step 514, the threshold setting are modified based on the results generated. The method 500 can stop at Step 516.

In some embodiments, the device and method disclosed herein automatically provide one or more predetermined ranges of threshold numbers when a user input a first quality control input. For example, a user can inspect/measure a length of a solder, such as 0.5 mm. Based on his/her experience, he/she enters the threshold values for +10% and −10% into the device of the present invention. The device automatically tests and generates a graph of False call ppm vs. defect escaped % at the data points 0.45 mm, 0.50 mm, and 0.55 mm. The graph shows numbers and the numerical relationship of the False call ppm and defect escaped % on all three data points. The user can based on the generated number of the False call ppm and defect escaped % to decide whether he/she wants to adjust the threshold value for next testing, such as +/−20%. A person of ordinary skills in the art appreciates that any other ranges of data points can be selected. Once a testing is performed, an a plot is made. The user is able to adjust the testing range/number based on the data relationships on the plot.

To utilize the quality control methods and devices, plurality of threshold setting are entered, which result in multiple data that are used to make a graph for showing the relationships of the results among the threshold settings. The methods and devices disclosed herein advantageously reduce time needed for programming the fine tuning of the quality control/inspection process with multiple testing output. Therefore, operators are able to make decisions more easily on threshold settings and optimizations based on the machine testing data/results.

In operation, an operational method includes choosing an algorithm for quality control, setting a threshold setting, performing one or more testings, receiving results, and generating a graphic presentation so that an operator can determine the relationships among the data points and predict the results of changing the threshold settings.

The present invention has been described in terms of specific embodiments incorporating details to facilitate the understanding of principles of construction and operation of the invention. Such reference herein to specific embodiments and details thereof is not intended to limit the scope of the claims appended hereto. It is readily apparent to one skilled in the art that other various modifications can be made in the embodiment chosen for illustration without departing from the spirit and scope of the invention as defined by the claims.

What is claimed is:

1. A method of performing quality control inspection comprising:
   a. entering plurality of threshold settings on an optical imaging inspection device configuring the optical imaging inspection device for a quality control inspection;
   b. generating graphic presentation showing a linear data relationship of a percentage of the defect escaped and a false call rate based on the data acquired by the optical imaging inspection device; and
   c. selecting a predetermined data of one of the percentage of the defect escaped or the false call rate based on a corresponding data of another on the linear data relationship.

2. The method of claim 1, wherein the false call rate comprises a rate of false call ppm (parts-per million).

3. The method of claim 1, wherein the quality control inspection comprises an automated optical inspection.

4. The method of claim 1, wherein the quality control inspection comprises an automated x-ray inspection.

5. The method of claim 1, wherein the quality control inspection comprises a solder paste inspection.

6. The method of claim 1, further comprising adjusting the threshold setting numbers based on the relationship.

7. The method of claim 6, wherein the relationship is substantially linear.

8. A quality control inspection system comprising:
   a. an optical imaging inspection device coupled with the computer;
   b. a first set of computer executable instructions stored in a computer configured to receive plurality of threshold setting numbers;
   c. a second set of computer executable instruction stored in the computer configured to operate the optical inspection element; and
   d. a graphic presentation generated by the computer showing a linear data relationship of a percentage of defects escaped and a false call rate using the detection data acquired by the optical imaging inspection device, wherein a predetermined data of one of the percentage of the defect escaped or the false call rate is selected for a next quality control inspection based on a corresponding data of another on the linear data relationship.

9. The system of claim 8, wherein the plurality of threshold setting numbers comprises at least three numbers.

10. The system of claim 8, wherein the optical inspection device comprises an automated optical inspection device.

11. The device of claim 8, wherein the optical inspection device comprises a solder paste inspection device.

12. The device of claim 8, wherein the optical inspection device comprises an automated x-ray inspection device.

13. The system of claim 8, further comprises a third set of computer executable instruction configured to plot data received from testing into data points on a chart showing the numeral relationship among the data points.

14. A method of inspecting an electronic circuit member comprising:
   a. requesting one or more inputs of at least two threshold settings on an optical imaging inspection device and configuring the optical imaging inspection device for a quality control inspection;
   b. performing a testing of electronic circuit inspection;
   c. receiving data of the testing;
   d. generating a graphic presentation showing a numerical linear relationship of a percentage of the defect escaped and a false call rate based on the data acquired by the optical imaging inspection device; and
   e. selecting a predetermined data of one of the percentage of the defect escaped or the false call rate based on a corresponding data of another on the linear data relationship.

15. The method of claim 14, wherein the data points are in a substantial linear relationship.

16. The method of claim 14, wherein the testing comprises an optical inspection.

17. The method of claim 14 further comprising selecting an algorithm of the testing.

18. The method of claim 14 further comprising adjusting the inputs of the at least two threshold settings.

* * * * *